United States Patent [19]
Shofner et al.

[11] Patent Number: 5,361,450
[45] Date of Patent: Nov. 8, 1994

[54] DIRECT CONTROL OF FIBER TESTING OR PROCESSING PERFORMANCE PARAMETERS BY APPLICATION OF CONTROLLED, CONDITIONED GAS FLOWS

[75] Inventors: Frederick M. Shofner; Mark G. Townes, both of Knoxville, Tenn.

[73] Assignee: Zellweger Uster, Inc., Knoxville, Tenn.

[21] Appl. No.: 999,226

[22] Filed: Dec. 31, 1992

[51] Int. Cl.$^5$ .............................................. D01B 3/04
[52] U.S. Cl. ............................... 19/66 R; 19/66 CC; 19/200
[58] Field of Search ............... 19/66 R, 66 CC, 200, 19/65 R, 98, 115 R, 65 A; 356/72

[56] References Cited

U.S. PATENT DOCUMENTS

| | | | |
|---|---|---|---|
| 3,881,222 | 5/1975 | Roberson | 19/66 R |
| 4,019,225 | 4/1977 | Nayfa | 19/66 R |
| 4,253,243 | 3/1981 | Whelan | 19/66 CC X |
| 4,512,060 | 4/1985 | Shofner | 19/200 |
| 4,527,306 | 6/1985 | Thannheiser | 19/66 |
| 4,613,781 | 12/1986 | Shofner | 19/200 |
| 4,686,744 | 12/1987 | Shofner | 19/200 |
| 4,726,096 | 2/1988 | Woods, Jr. | 19/66 CC |
| 4,943,300 | 7/1990 | Vinnikov | 19/66 CC X |
| 5,121,522 | 6/1992 | Leifeld et al. | 19/66 |
| 5,138,879 | 8/1992 | Shofner et al. | 73/160 |
| 5,157,910 | 10/1992 | Artzt et al. | 19/66 R X |

OTHER PUBLICATIONS

*Electro-Optical Trash Particle Counting and Sizing,* Anton Schenek, Anja Schleth, Mark. G. Townes, Frederick M. Shofner, Manfred Frey and Walter Schnelter. (undated).

*Utilization of the Complete Fiber Length Distribution From the Advanced Fiber Information System,* Frederick M. Shofner, Michael E. Galyon, Manfred Frey, Walter Schnelter and C. Kenneth Bragg. (undated).

"Possibilities of Direct Conditioning in Rotor Spinning", International Textile Bulletin Yarn Forming, 3rd Quarter 1990.

"Fiber Testing USTER AFIS-T Measuring Trash and Dust Particles in Cleaning and Carding" Zellweger Uster, Sep. 1991.

"An Overview of The Advanced Fiber Information System" Zellweger Uster. Mar., 1990.

"Advanced Fiber Information System: A New Technology for Evaluating Cotton", Shaffner Technologies, Inc. Dec. 1988.

"Trash Testing A Guide to USTER MDTS 3 and USTER AFIT-T", Zellweger Uster, 1991.

*Primary Examiner*—Clifford D. Crowder
*Assistant Examiner*—John J. Calvert
*Attorney, Agent, or Firm*—Luedeka, Neely & Graham

[57] ABSTRACT

Conditioned gas flows are applied at various critical locations in instruments and apparatus for testing and processing textile fibers, such as cotton. In the context of test instruments, a standard test zone environment (which becomes part of the test record) is effected by the introduction of controlled conditioned gas flows directly into a testing zone, including into testing instruments themselves. In the context of processing apparatus, direct control of processing performance parameters is effected by "controlling parameters", which are in turn effected by the application of conditioned gas flows. A plurality of "performance parameters", which may be in conflict with each other, may be controlled in accordance with a predetermined compromise control strategy, carried out by feedback or feedforward control systems implementing modern statistical control approaches.

30 Claims, 10 Drawing Sheets

DIRECT CONTROL OF FIBER TESTING OR PROCESSING PERFORMANCE PARAMETERS BY APPLICATION OF CONTROLLED, CONDITIONED GAS FLOWS

FIELD OF THE INVENTION

The invention relates generally to the testing and processing of textile fibers, such as cotton, used in the formation of yarn. The invention more particularly relates, for fiber testing, to test zone environmental control and, for fiber processing, to the direct control of processing performance parameters through the control of controlling parameters. Both are effected by application of conditioned gas flows at various critical locations. In the context of fiber testing instruments, the invention provides improved "standard" environments for various test parameters such as trash content, nep content, and short fiber content. In the context of fiber processing, the invention results in optimal control of a plurality of processing performance parameters, such as trash content, nep content and short fiber content.

BACKGROUND OF THE INVENTION

In order to optimize yarn processing performance and end-product quality, tests are commonly applied to textile entities which include fibers and undesirable entities such as neps and trash. Zellweger Uster, Inc., Knoxville, Tenn.; Uster, Switzerland; and others manufacture a wide range of fiber and yarn testing instruments, both of the laboratory type and the on-line process control type, that are increasingly used by textile producers worldwide.

In today's highly competitive and quality conscious marketplace the use of these instruments in laboratory testing and process monitoring has gone beyond simply giving the user a competitive advantage. Their use has, in the area of classing cotton for loan eligibility, been dictated by the U.S. government, and has otherwise become a requirement of business survival. Raw materials are procured and lots of finished goods are accepted or rejected based on fiber and yarn properties as determined by these instruments. For example, nearly 100% of U.S. cotton bales are classified as to fiber length, fiber strength/elongation, color, micronaire, and trash content by HVI (High Volume Instrumentation) systems (manufactured by Zellweger Uster, Inc., Knoxville, Tenn.), thus replacing the traditional human cotton classer. The measured results determine the monetary value of the bale and serve as a first process control measurement for spinning mills.

Increased demands on fiber properties, such as increased fiber cleanliness and decreased neps and short fiber content, have brought increased demands for instruments that measure those properties and increased expectations for the precision and accuracy of the measurements. For instance, the AFIS (Advanced Fiber Information System), also manufactured by Zellweger Uster, Knoxville, Tenn. and described in the papers "Utilization of the Complete Fiber Length Distribution from the Advanced Fiber Information System" and "Electro-Optical Trash Particle Counting and Sizing", Bremen Cotton Conference, Bremen, Germany, and in various copending patent applications referenced hereinbelow, can make measurements of fiber trash content, fiber length distributions (including short fiber content), and fiber nep levels. MANTIS, also manufactured by Zellweger Uster, Knoxville, Tenn., can measure single fiber breaking tension, elongation, and diameters. MANTIS is described in U.S. Pat. No. 5,138,879.

Both instrument and process machinery manufacturers have long known that the microenvironment surrounding the test or processing zones can have a profound effect on fiber measurement and processing performance parameters. For example, cotton fiber is mostly cellulose and is highly hygroscopic. Increasing moisture content increases strength, causes fiber swelling, aggravates cleaning and sugar-related "stickiness", and reduces electro-static effects. These and other changes in fiber behavior associated with the test or processing micro-environment are well known and are utilized to a limited extent by textile fiber processors by controlling the macroenvironment. In ginning, for example, moisture content in the fiber is purposefully reduced to about 5% or below by driers. This allows more effective cleaning but, along with other effects, weakens the fibers and aggravates static charge problems. On the other hand, in weaving rooms where fiber and associated yarn strength is critical, the relative humidity may be held as high as 85%, corresponding to a moisture content of about 9% in the yarn.

However, precise macroenvironmental control in testing laboratories or manufacturing facilities is difficult, expensive and, in most cases, far less effective than desired. A large controlled space offers a buffer to small perturbations in, for example, humidity, temperature, and ion concentration, but is slow to respond to control actions. It is common to find very expensive (millions of dollars for large production areas) macroenvironmental control systems which, indeed, control relative humidity and temperature to $\pm 2\%$, and $\pm 1°$ F. but, unfortunately, allow the test or production zone to fluctuate $\pm 10\%$ and $\pm 5°$ F.

As discussed in Shofner U.S. Pat. Nos. 4,512,060, 4,631,781 and 4,686,744, increasing demands are being placed on fiber properties as textile processing machinery production rates increase and as the tolerances of textile processing machinery for variances in the fiber properties decrease. Current production and harvesting methods inherently entrain more foreign matter content into cotton fiber, for example, such that the ginning and cleaning actions required to achieve a given percentage of foreign matter content are increasing. Increased cleaning is always at the expense of fiber loss and damage. The incompatibility between the goals of clean versus undamaged fiber increases the difficulties faced by producer, ginner, merchant and spinner. Providing clean and undamaged fiber is a major, would-wide problem and improved processing methods and apparatus are urgently needed, especially in the areas of test zone and process zone environmental control.

As generally recognized in the above-identified Shofner U.S. Pat. Nos. 4,512,062, 4,631,701 and 4,686,744, it is advantageous to condition air or other gas, such as transport gas, in both processing add testing machines for improved machine operation. For example, as disclosed in those patents, there can be a preferred state of the fiber with regard to humidity and static charge for a particular operation, such as a cleaning operation. It is further recognized in those patents that parameters such as humidity and electrostatic charge of the fiber may be different at each of a plurality of different processing stages. Although temperature, humidity and static charge are perhaps the most obvious parameters of transport gas which may be conditioned, others are possible. For example, the above-identified patents also disclose the conditioning of transport gas as to humidity, temperature, pressure, gas composition, free charge concentration, static charge, radioactive particle concentration, velocity and pressure fluctuations.

Other examples of controlling temperature and humidity in particular in a textile processing machine are disclosed in Thannheiser U.S. Pat. No. 4,527,306 and Leifeld et al U.S. Pat. No. 5,121,522. Those patents describe systems in which pneumatic transport air within a textile processing machine is conditioned with respect to temperature and humidity, employing a feedback control system. U.S. Pat. No. 5,121,522 in particular discloses a system for measuring "humidity" and temperature of fiber tufts directly for use in controlling an air conditioning system. As noted in those patents, one reason for control is that if, for example, the transport air is too dry, electrostatic charges can cause undesirable fiber accumulations within the equipment. On the other hand, if the transport air is too humid, balling of fiber tufts can result.

Thus, the control of moisture content in fiber processing is well known. Further, under the influence of conditioned gas flow, it is known that single fibers can reach a point of equilibrium (e.g. with respect to moisture content) almost instantaneously, whereas tufts or masses of fibers require longer periods of time to reach equilibrium.

There are, however, a number of conflicting considerations, which have not heretofore been effectively addressed. It is known, for example, that fiber is best cleaned when fiber moisture content is relatively low, for example, below 5%. It is also known that the strength of cotton fiber is a maximum at a relatively higher moisture content, for example, above 5%. Strength of cotton fiber affects the degree of undesirable fiber breakage during processing operations.

SUMMARY OF THE INVENTION

Accordingly, it is a broad object of the invention to improve the overall performance of fiber testing instruments and processing machines through the application of appropriately controlled conditioned gas flows.

Briefly stated, and in accordance with a first overall aspect of the invention, it is recognized that optimum maintenance of a standard test zone environment of 70° F. and 65% relative humidity, as prescribed by the American Society for Test Materials (ASTM), can be effected by the introduction of controlled conditioned gas flows directly into the immediate testing zone, including into testing instruments themselves.

By way of example, and not limitation, test zone environmental parameters which may be controlled by application of controlled conditioned gas flows include humidity, temperature, velocity, pressure, velocity fluctuations, pressure fluctuations, gas composition, free charge concentration, static charge, and radioactive particle concentration. Suitable sensors exist for measuring each of these test zone parameters for application in a feedback control system.

Moreover, in accordance with the invention it is recognized that optimum test zone environmental control may be effected by the simultaneous introduction of controlled conditioned gas flows into a plurality of testing zones in, for example, a HVI (High Volume Instrumentation) test line.

In accordance with a more particular aspect of the invention, a method for controlling the immediate test zone environment in a testing instrument, for example a strength testing instrument, includes the steps of measuring at least one test zone environmental parameter, such as a test zone environmental parameter presented hereinabove, and then controlling the test zone environmental parameter to a predetermined level or value by deliberately applying, during testing, a gas flow conditioned to maintain that environmental parameter at the predetermined value.

Similarly, the invention provides a method for controlling the test zone environment in an instrument having a plurality of testing zones, one of which may be a nep testing zone, wherein, for each of the testing zones, at least one test zone environmental parameter is measured, and the environmental parameter for each of the testing zones is controlled by deliberately applying, at a point appropriate for the particular testing zone, a gas flow conditioned to maintain that environmental parameter at a predetermined value.

The invention also provides a method for post-test control of fiber properties in preparation for further processing. The method includes the steps of measuring at least one fiber property, such as moisture content, and then controlling the fiber property to a predefined level by deliberately applying, after testing, a gas flow conditioned to bring that fiber property to the predetermined value.

A corresponding apparatus in accordance with the invention includes a fiber testing instrument, such as an AFIS, a hood for directing conditioned air onto the instrument surface, and a means for directing conditioned air into the interior components of the instrument. A sensor is provided for measuring at least one environmental parameter in the testing zone, and there is a conditioned supply system for applying a gas flow to the testing zones. A feedback control system is connected to the sensor and to the conditioned supply system for maintaining the test zone environmental parameter at a predetermined value by controlling the environmental parameter of the applied gas flow.

Other apparatus in accordance with the invention include fiber testing instruments having a plurality of testing stages and associated testing zones. A sensor is provided for each testing zone for measuring at least one test zone environmental parameter, and there are respective conditioned supply systems for applying, at a point appropriate for each zone, a gas flow conditioned such as to effect test zone environmental parameters. A feedback control system is connected to the sensors and to the conditioned supply system for maintaining, at a predetermined value, the test zone environmental parameter for each of the testing zones by controlling the environmental parameters of the applied gas flow.

Another apparatus in accordance with the invention is a movable conditioning unit capable of supplying differently conditioned air flows to a multiplicity of testing or fiber processing zones. The unit includes, but is not limited to, an air filter, blower, and cooling coil that deliver cool, dry, and filtered air to numerous individually controlled conditioning modules. In the conditioning modules heat, moisture, and charged ions are added to, or withheld from, the air stream as it moves into flexible conduits and is delivered to appropriate testing zones. Based on feedback from sensors in the testing zones, a computer based control unit adjusts the temperature, moisture content, ion content, and flow rate in each conditioning module such that properly conditioned air is delivered to each test zone.

In accordance with a second overall aspect of the invention, it is recognized that direct control of processing performance parameters, not just the processing zone environment, may be effected by means of what are herein termed "controlling parameters" effected by the application of conditioned gas flows. Moreover, a plurality of "processing performance parameters", which may be in conflict with each other, may be controlled in accordance with a predetermined compromise control strategy, carried out by feedback or feedforward control systems implementing modern statistical control approaches.

By way of example, and without limitation, processing performance parameters include trash content, nep content, short fiber content, trash removal efficiency, nep removal efficiency, short fiber removal efficiency, and machinery production efficiency. Suitable sensors exist for measuring each of these performance parameters for application in a feedback control system. As already noted, these processing performance parameters may be in conflict with each other. For example, lowering moisture content to achieve improved (lower) trash content can result in degraded (increased) short fiber content as a result of fiber breakage within the machine. A particular compromise among the conflicting processing performance parameters exists in many given situations which results in the highest sales value of the resultant product.

By way of example, and not limitation, controlling parameters which may be effected by application of conditioned gas flows include humidity, temperature, velocity, pressure, velocity fluctuations, pressure fluctuations, gas composition, free charge concentration, static charge, and radioactive particle concentration.

Moreover, in accordance with the invention it is recognized that the relevant processing performance parameters and consequent controlling parameters differ at different stages in a textile processing apparatus, and in accordance with the invention these are separately controlled.

In accordance with a more particular aspect of the invention, a method for processing fiber in a machine, for example a carding machine, includes the steps of measuring at least one processing performance parameter, such as a machine performance parameter from the list presented hereinabove, and then controlling the processing performance parameter by deliberately applying, during processing, a gas flow conditioned by at least one controlling parameter, such as the controlling parameters in the list presented hereinabove. Preferably, a plurality of processing performance parameters are controlled in accordance with a predetermined compromise control strategy.

Similarly, the invention provides a method for processing fiber in a machine having a plurality of processing stages, one of which may be a carding stage, wherein, for each of the processing stages, at least one processing performance parameter is measured, and the processing performance parameter for each of the processing stages is controlled by deliberately applying, at a point appropriate for the particular processing stage, a gas flow conditioned by at least one controlling parameter. Preferably, for at least one of the processing stages, a plurality of processing performance parameters are controlled in accordance with a predetermined compromise control strategy.

A corresponding apparatus in accordance with the invention includes a fiber processing machine, such as a carding machine, and a conveying system for supplying fiber material to the processing machine. A sensor is provided for measuring at least one processing performance parameter of the fiber processing machine, and there is a conditioned supply system for applying a gas flow conditioned by at least one controlling parameter which affects the processing performance parameter. A feedback control system is connected to the sensor and to the conditioned supply system for controlling the processing performance parameter by controlling the controlling parameter. Preferably, the feedback control controls a plurality of processing performance parameters in accordance with a predetermined compromise control strategy.

Another apparatus in accordance with the invention includes a fiber processing machine having a plurality of processing stages, and a conveying system for supplying fiber material to the fiber processing machine. A sensor is provided for each of the processing stages for measuring at least one processing performance parameter, and there are respective conditioned supply systems for applying, at a point appropriate for each stage, a gas flow conditioned by at least one controlling parameter which affects the processing performance parameter for the particular stage. A feedback control system is connected to the sensors and to the conditioned supply systems for controlling the processing performance parameter for each of the processing stages by controlling the controlling parameter for the particular stage. Preferably, for at least one of the processing stages, a plurality of processing performance parameters are controlled in accordance with a predetermined compromise control strategy.

BRIEF DESCRIPTION OF THE DRAWINGS

While the novel features are set forth with particularity in the appended claims, the invention, both as to organization and content, will be better understood and appreciated, from the following, taken in conjunction with the drawings, in which:

DETAILED DESCRIPTION OF PREFERRED EMBODIMENTS

Test Zone Environmental Control

Figure 1:
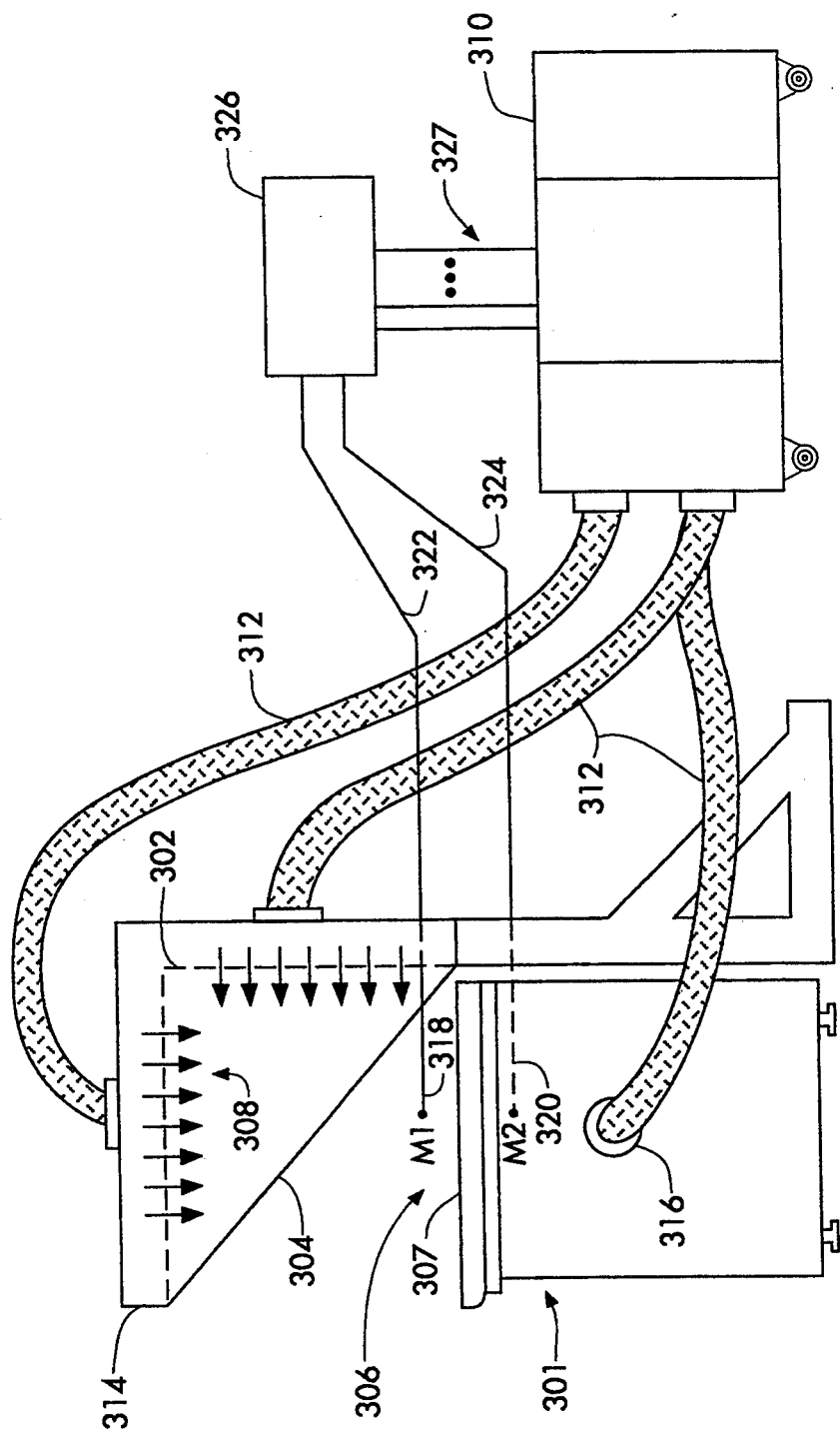
FIG. 1 depicts test zone environmental control apparatus for a generic fiber testing instrument.

FIG. 1 illustrates test zone environmental control apparatus 300 for a generic fiber testing instrument 301.

Controlled conditioned gas, air in this case, is supplied from separate control 326 and conditioning 310 units through flexible tubing 312 to a hood 314 and to the inside of the instrument through fitting 316. The fiber testing instrument 301 may be an Advanced Fiber Information System (AFIS), High Volume Instrument (HVI), Microdust and Trash Monitor (MTM), or MANTIS, all manufactured by Zellweger Uster, Inc., Knoxville, Tenn., or the like. Application of test zone environmental control is described below for HVI and AFIS.

The controlled, conditioned gas flow is provided to a test zone 306 through perforated distribution plates 302. Test zone 306 is generally above the top surface 307 of instrument 301 but, for many tests, the sensors are below surface 307 or inside the instrument, in which case the controlled, conditioned gas flow is supplied through fitting 316. A partial list of representative conditioned gas flow parameters is: flow rate 300 cubic feet per minute, relative humidity 65%, dry bulb temperature 70° F., dust concentration less than 25 micrograms per cubic meter, face velocity 308 at the distribution plates less than 100 feet per minute, neutral ion content, and less than 60 dBA noise or pressure fluctuations.

It will be appreciated that 65% RH and 70° F. are standardized test conditions established by the industry through the American Society for Test Materials (ASTM), Philadelphia, Pa. It will be further appreciated that the hood 314 enables better control of that part of the test zone above the top surface 307 than does the commonplace macroenvironmental control of the entire test laboratory. Still further, supplying controlled, conditioned gas to the internal microenvironment zones of instrument 301, wherein the fibers are actually tested, enables the best control. Thus, the hood 314 for supplying controlled conditional gas flows lies in design concept between macroenvironmental control of the testing room and microenvironmental control of the test zone.

Referring again to FIG. 1, monitoring means M 318 and M 320 represent sensors for each of the gas conditions to be controlled. Representative signal lines 322 and 324 connect sensors M 318 and M 320 to control unit 326. Only two monitoring sensors M 318 and M 320 are shown in FIG. 1, but it will be understood that a multiplicity of monitoring sensors are used. Control unit 326 contains appropriate electronics and a computer which control the conditions of gas supplied by conditioning unit 310 through tubing conduits 312. Not shown are conduits returning the gas from the instrument 301 to the conditioning unit 310. The control unit 326 is connected to conditioning unit 310 by signal and control lines 327. Control unit 326 and conditioning unit 310 are shown as separate entities in FIG. 1 for clarity but they, of course, can be integrated into one enclosure. In some cases, it is desirable to integrate both into the instrument 301.

Figure 2:
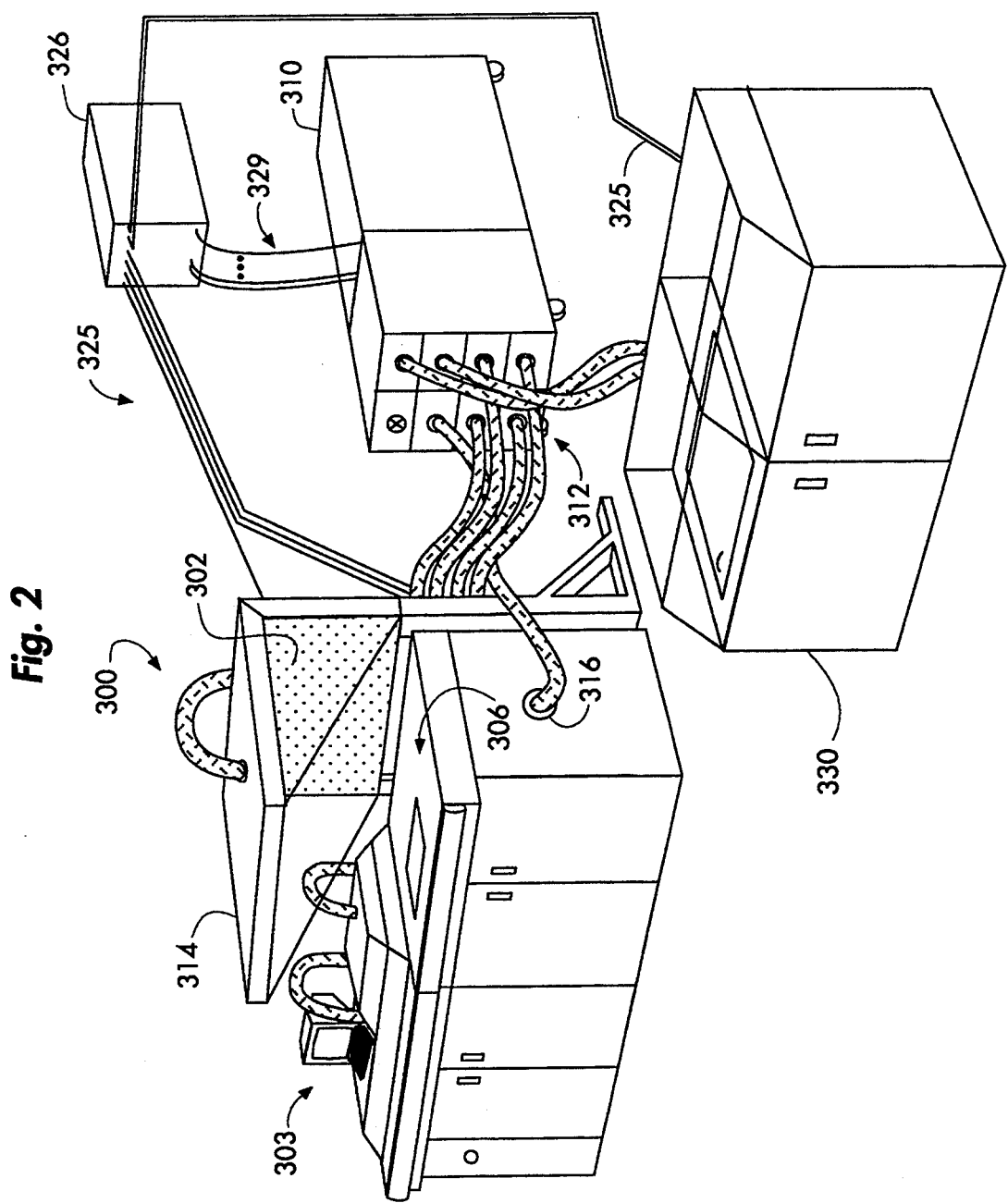
FIG. 2 depicts the apparatus of FIG. 1 applied to an HVI 900A instrument.

FIG. 2 is a pictorial view of the generic apparatus of FIG. 1, but with application to an HVI 900A instrument 303. Seven supply conduits 312 are shown coming out of conditioning unit 310, along with a multiplicity of monitor signal lines 325 and signal and control lines 329, coming out of control unit 326. Clear plastic side shields 304, for example made of Lexan, are seen in both FIGS. 1 and 2. FIG. 2 also shows that two supply conduits 312 connect conditioning unit 310 to sample conditioning chamber 330, along with two signal and control lines 325. Sample conditioning chamber 330 serves to precondition samples prior to testing in the more precisely controlled test zone environment of apparatus 300.

Figure 3:
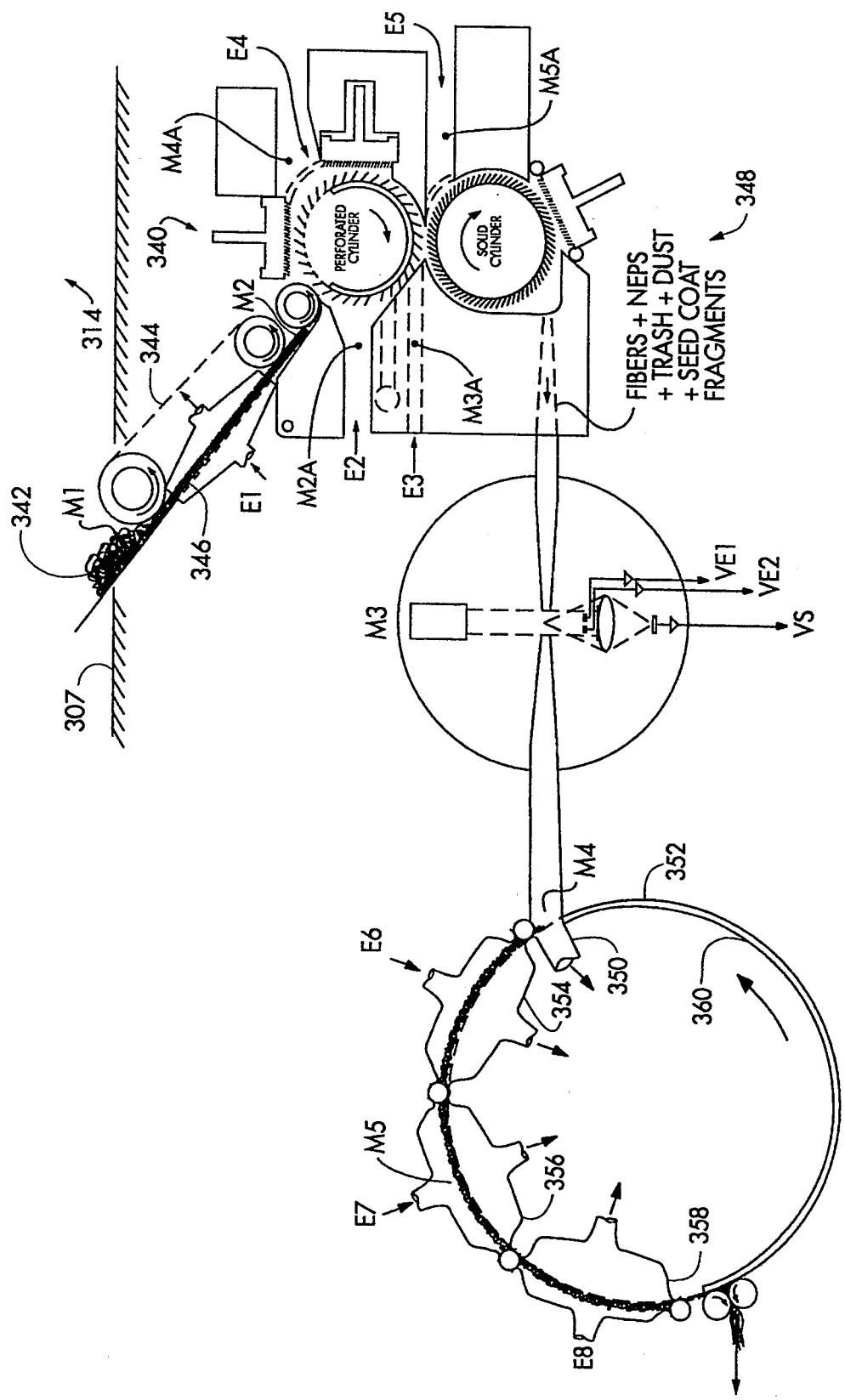
FIG. 3 depicts microenvironment control.

Whereas FIGS. 1 and 2 describe an improvement in test zone environmental control involving macroenvironment control, FIG. 3 describes an embodiment of the invention to microenvironment control, specifically, to the inner working parts or test zone of the fiber individualizer 340 of an AFIS. (AFIS is one of the generic instruments 301 represented in FIG. 1.) It is possible to employ the hood 300 with the internal microenvironment control now disclosed. AFIS top surface 307 in FIG. 3 is the same surface 307 as generically represented in FIG. 1.

A brief overview of AFIS operation is in order here to more fully disclose our methods and apparatus. More complete descriptions may be found in Shofner U.S. Pat. Nos. 4,512,060, 4,631,781 and 4,686,744 and in copending Shofner et al applications Ser. No. 07/493,961, filed Mar. 14, 1990, entitled "Electro-Optical Methods and Apparatus for High Speed, Multivariate Measurement of Individual Entities in Fiber or Other Samples" (AFIS sensor) and Ser. No. 07/762,613, filed Sep. 19, 1991, entitled "Topological Map-Maker".

In the AFIS of FIG. 3, a fiber sample 342 is introduced between perforated feed belt 344 and perforated feed plate 346. Sensor set M1 responds to moisture content or temperature and, in combination with sensor set M2, causes the conditioned gas supplied to point E1 to be controlled so that M2 achieves preset or desired values. Alternatively, conditions E1 can be chosen to be, for example, ASTM testing standards of 65% and 70° F.

It will be appreciated that there are subtle but important differences between these two control strategies. When the objective is achieving reproducible test results, the entire instrument and especially the microenvironment of the internal test zone are advantageously operated under standard conditions which become part of the test record. When the objective is achieving superior processing performance, it is better to directly control the fiber properties or the processing parameters, as explained below. Accepting, to meet fiber testing objectives, that the entire test zone environment should be controlled to standard conditions, to be made part of the test record, we now complete the explanation for the AFIS.

Test zone environmental control points E1, E2, E3, E4 and E5 are all supplied with whatever air conditions are required, not necessarily the same air, to enable controlling to standard conditions. Conditioning unit 310, described hereinbelow, and control unit 326, described above, enable this. Since the fiber individualizer 340 operates under negative pressure, such that the flows shown at each E1-E5 point are inherently pulled into the machine, it is a straightforward matter to supply the conditioned air. While this completes the description of microenvironmental control for AFIS, it will be appreciated that the objective of controlling the test environment is to enable operating on the fibers in recordable standard conditions for subsequent testing by sensor M3.

Suction applied to conduit 350 causes the individualized entities 348 to be deposited on moving screen 352. Except for regions at conduit 350 and at other suction plenums 354, 356 and 358, screen 352 is blocked by internal sleeve 360. Conditioned gas flow from sources E6, E7 and E8 is drawn through the screen 352 by suction plenums 354, 356, 358. Individualized entities after individualizer 340 and sensor M3 are further examined at monitoring station M5, for which either the test zone environment is controlled by E6 and E7 or certain properties of the entities are controlled. Monitoring means M5 are preferably image analysis, as disclosed in concurrently-filed Shofner et al application Ser. No. 07/999,007, filed Dec. 31, 1993, entitled "Acquisition, Measurement, and Control of Thin Webs of In-Process Textile Materials".

Figure 4:
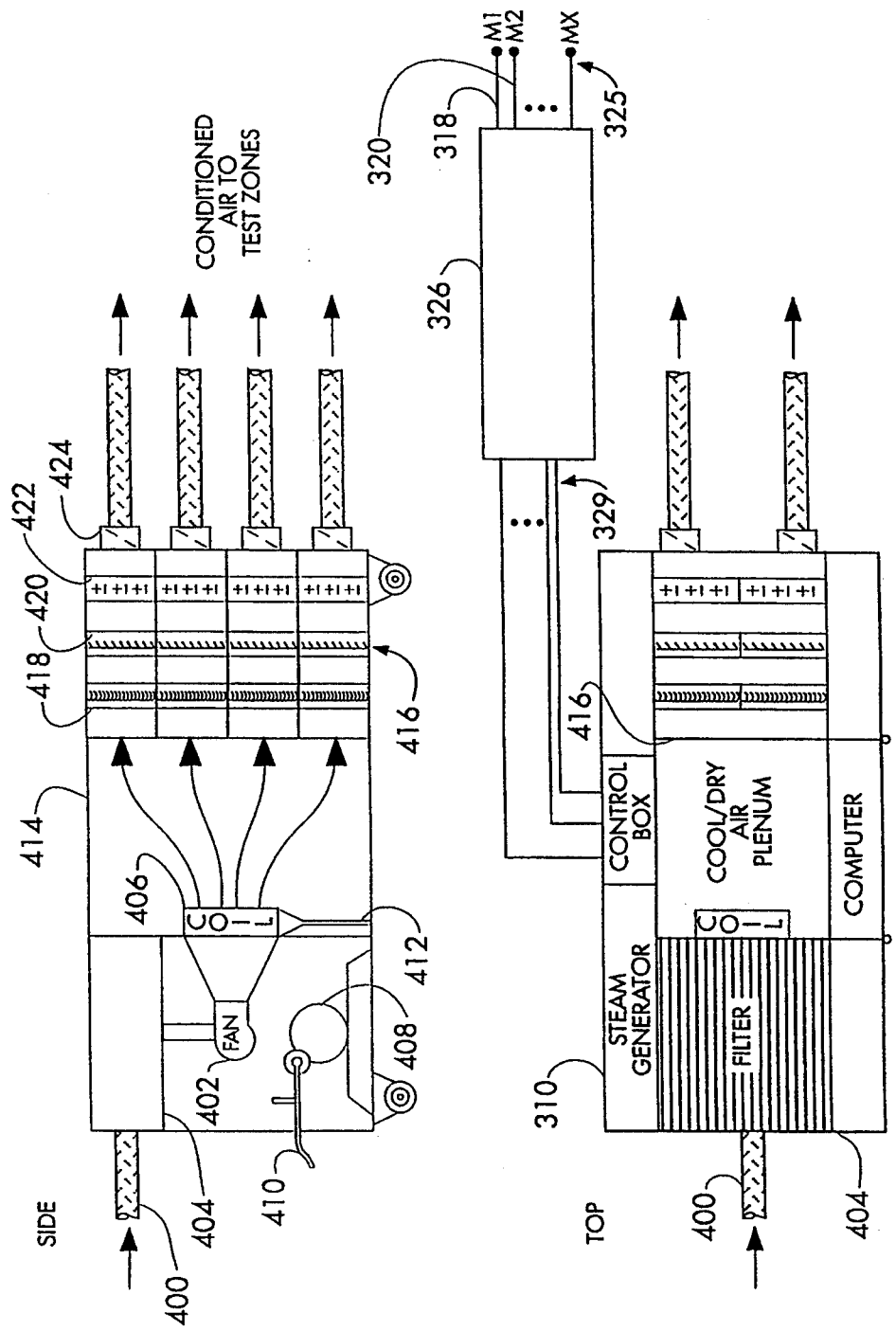
FIG. 4 depicts control and conditioning units for test zone environmental control.

Before disclosing the process zone environment control embodiment of our invention, we complete the disclosure of test zone environment control by referring to FIG. 4, wherein separate control 326 and conditioning units 310 are shown. Monitoring sensors M1, M2, etc., and control electronics within control unit 326 are well known in the art. Greater detail is now provided for conditioning unit 310.

Air is drawn into inlet 400 by fan 402 and first passes through dust filter 404 which might be a HEPA (High Efficiency Particle Arrester) filter. The discharge of fan 402 then passes over refrigeration coils 406. Refrigeration is provided by compressor system 408. Water is supplied at inlet 410 for condenser cooling and for steam humidification. A cooling water and condensate drain 412 is shown. The cooled and dried air in plenum 414 is then divided among eight final conditioning modules 416.

Each conditioning module 416 has a reheat coil 418, a steam bar 420, and ion grid 422, and a flow control damper 424. Each of the conditioning elements 418–424 is separately controlled by control unit 326 in response to signals delivered on lines 325 from individual monitoring sensors M described above.

When the test zone environment under the influence of one of the conditioning modules is itself controlled, the monitoring sensors respond to one or more of humidity, temperature, velocity, pressure, velocity fluctuations, pressure fluctuations, gas composition, free charge concentration, static charge, and radioactive particle concentration, or the like and the control system 326 causes the output of that module to be adjusted to the desired values for the test zone under the influence of that module. This is direct control of the fiber testing zone parameters. Representative microenvironment test zones are E1–E8 in FIG. 3, and representative monitoring points for the zones are M1–M5 and M2A–M5A.

When the parameters of the processing machinery performance are controlled by application of conditioned gas flows, and the monitoring sensors M respond thereto, this is direct control of processing performance parameters, not of the processing environment, and is a further embodiment of our invention whose disclosure we now provide.

Process Zone Environmental Control

Figure 5:
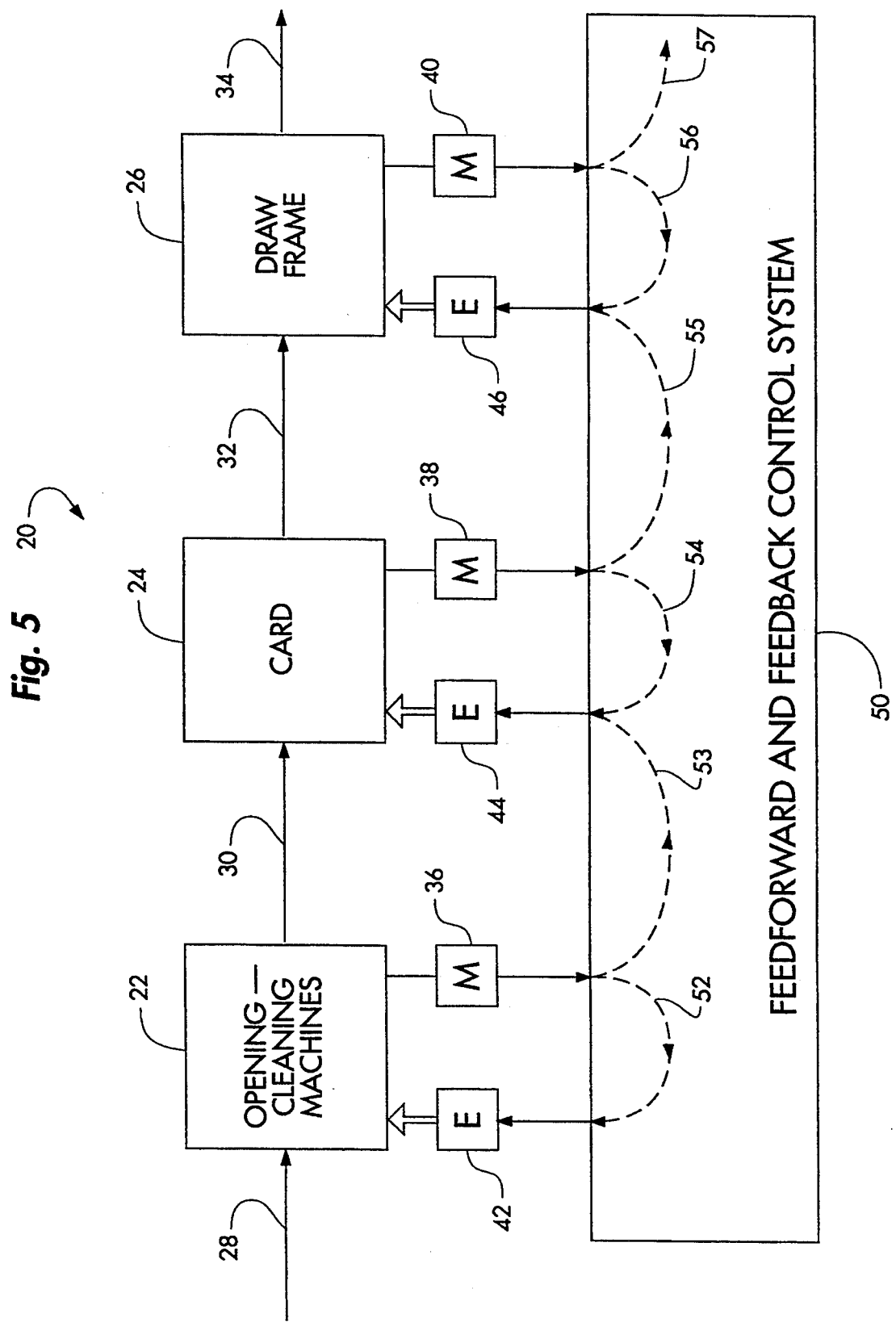
FIG. 5 is a block diagram of a control system in accordance with the invention connected to a multi-stage fiber processing machine shown in highly schematic form.

Referring now to FIG. 5, depicted in highly generalized form is a fiber processing machine set 20 having a plurality of sequential processing stages, represented as opening-cleaning machines 22, cards 24 and draw frames 26. Fiber material in the bale state 28 is opened, cleaned and converted by machinery line 22 into the tuft state 30. The tufts of fibrous material exit the opening-cleaning line 22 and are formed into a mat 30, which then enters the card 24, emerging as sliver 32, which enters the draw frame 26, emerging from the draw frame 26 as blended sliver 34.

The overall machine set 20 is representative not only of the processing of fiber starting with bale opening and extending through the drawing operation, but is also representative of continuing machine processes in the production of yarn, including draw frames, combers, roving machines, and rotor and/or ring spinning frames.

Concurrently-filed Shofner et al application Ser. No. 07/999212, Dec. 31, 1992 entitled "Methods of Optimally Controlling Fiber Processing Machines" lists and discusses yarn manufacturing machinery, describes the "machinery characteristics" of the rotor spinbox in particular, and provides novel methods for optimal control of fiber processing machinery in general. Machinery characteristics relate processing performance parameters at the various machinery outputs as they are affected by input parameters and machinery operational settings. Those disclosures are incorporated herein by reference. It is specifically noted that the instant disclosures for controlling processing performance parameters with conditioned gas flows constitute a further application of the above-referenced invention.

Associated with each of the machinery stages 22, 24 and 26 is a measuring station M, shown as representative sensors 36, 38 and 40, as well as an environmental control station E, shown as representative conditioned gas supply systems 42, 44 and 46.

The sensors 36, 38 and 40 are each known devices, and do not themselves constitute the subject matter of this invention. In general, the sensors 36, 38 and 40 measure processing performance parameters, such as trash content, nep content, short fiber content, and related parameters such as trash removal or generation efficiency, nep removal or generation efficiency and short fiber removal or generation efficiency. In general, the machines can both remove and generate and the efficiency can be less than unity (removal) or greater than unity (generation). For example, a poorly adjusted card can break up trash particles, create more neps than it removes, and break fibers. Although a single sensor 36, 38 and 40 is shown associated with each of the stages 22, 24 and 26, it will be appreciated that each of the indicated sensors is representative of a plurality of sensors which may be associated with each particular stage. Appropriate sensors may also be provided to measure various processing efficiencies, including production efficiency.

The conditioned gas supply systems 42, 44 and 46 serve to apply conditioned gas flows conditioned by at least one controlling parameter, such as humidity, temperature, velocity, pressure, velocity fluctuations, pressure fluctuations, gas composition, free charge concentration, static charge, and radioactive particle concentration. Although the conditioned gas supply systems 42, 44 and 46 are shown as separate elements, it will be appreciated that the separate elements depicted may comprise elements of an overall air supply system, for example having a single blower, having a plurality of branch ducts, with individual control elements such as heaters, humidifiers, controlled dampers and/or filters in the individual ducts.

In accordance with the invention, and as is described hereinbelow in greater detail with reference to FIGS. 6–9 in the context of a card, such as the card 24, the machine performance parameters as measured by the sensors 36, 38 and 40 are controlled by controlling the controlling parameters delivered by the conditioned gas supply systems 42, 44 and 46. Accordingly, there is provided a feedback control system, generally designated 50, which receives outputs of the sensors 36, 38 and 40 to derive signals for controlling the conditioned gas supply systems 42, 44 and 46. Individual feedback loops are indicated in highly schematic fashion as dash lines 52, 54 and 56. Individual feedforward lines are 53, 55 and 57.

Figure 6:
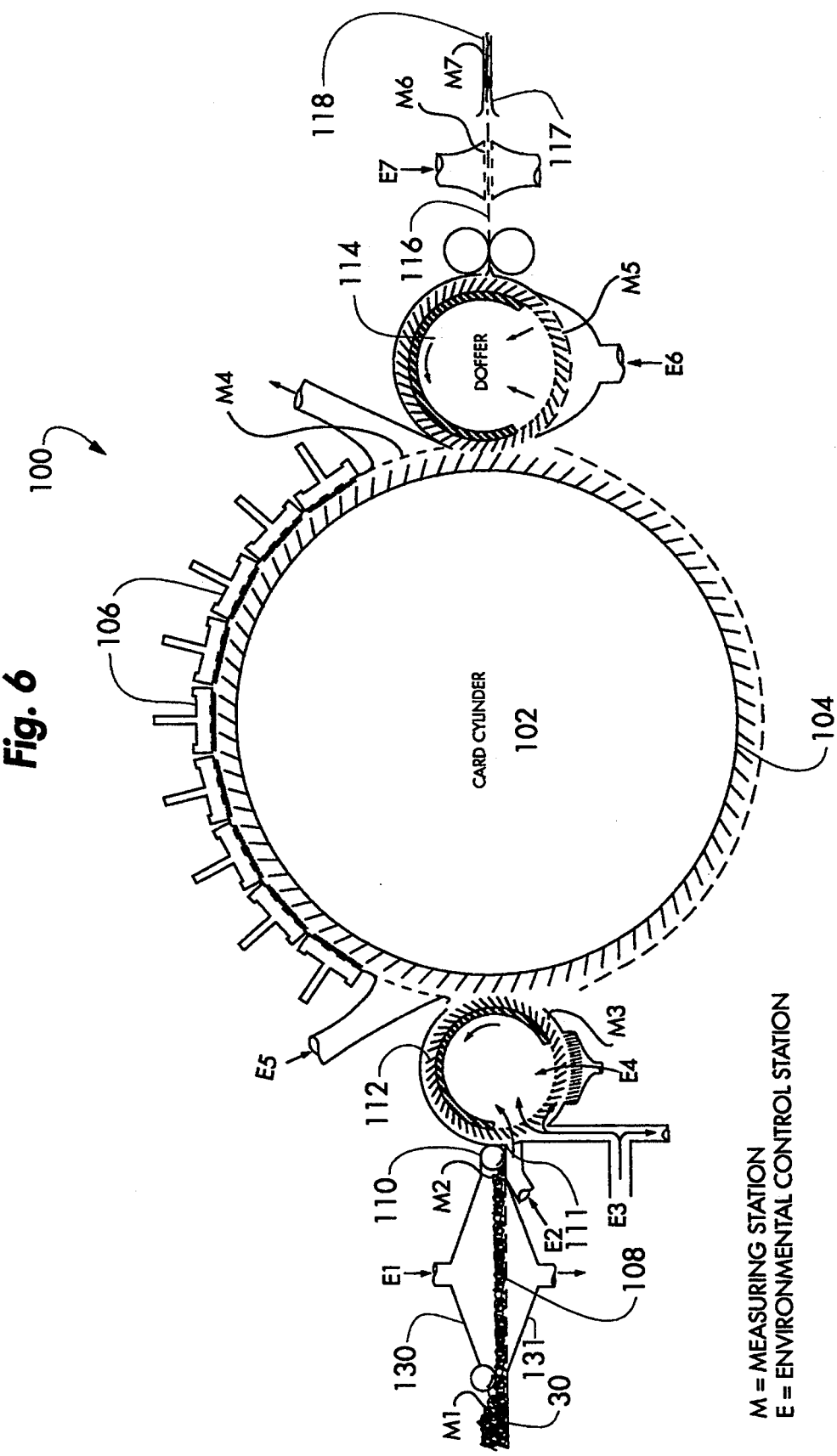
FIG. 6 depicts a carding stage.

Although not illustrated in FIG. 6, it will be appreciated that each of the conditioned gas supply systems 42, 44 and 46 may include its own feedback loop. For example, if the feedback control system 50 directs one of the conditioned gas supply systems 42, 44 or 46 to maintain a given percentage relative humidity at a particular supply point, then that particular conditioned gas supply system may itself include a relative humidity sensor which, through feedback control, directs the operation of a humidifier element, such as a water spray.

It will further be appreciated that the feedback loops 52, 54 and 56 are greatly simplified, in that each is shown connected to a single one of the sensors 36, 38 and 40 whereas, in accordance with the invention, the feedback control system 50 may take into account a plurality of conflicting machine performance parameters, and implement an overall optimal control strategy employing modern statistical control methodology to achieve an overall best compromise.

It may also be noted that, while the diagram of FIG. 5 implies a processing performance parameter sensor at the output of each stage, and a conditioned gas supply system at the input of each stage, such is not necessarily the case in any given embodiment. Thus, a processing performance parameter sensor may be applied wherever appropriate. Such may be within a stage, at the immediate exit of the stage, or downstream of the particular stage.

Similarly, a conditioned gas supply may be applied to fiber material as it is conveyed to a particular processing stage, to the fiber immediately as it enters the particular processing stage, to fiber within the particular processing stage, or even to fiber upstream of a particular fiber processing stage, or any combination.

Figure 7:
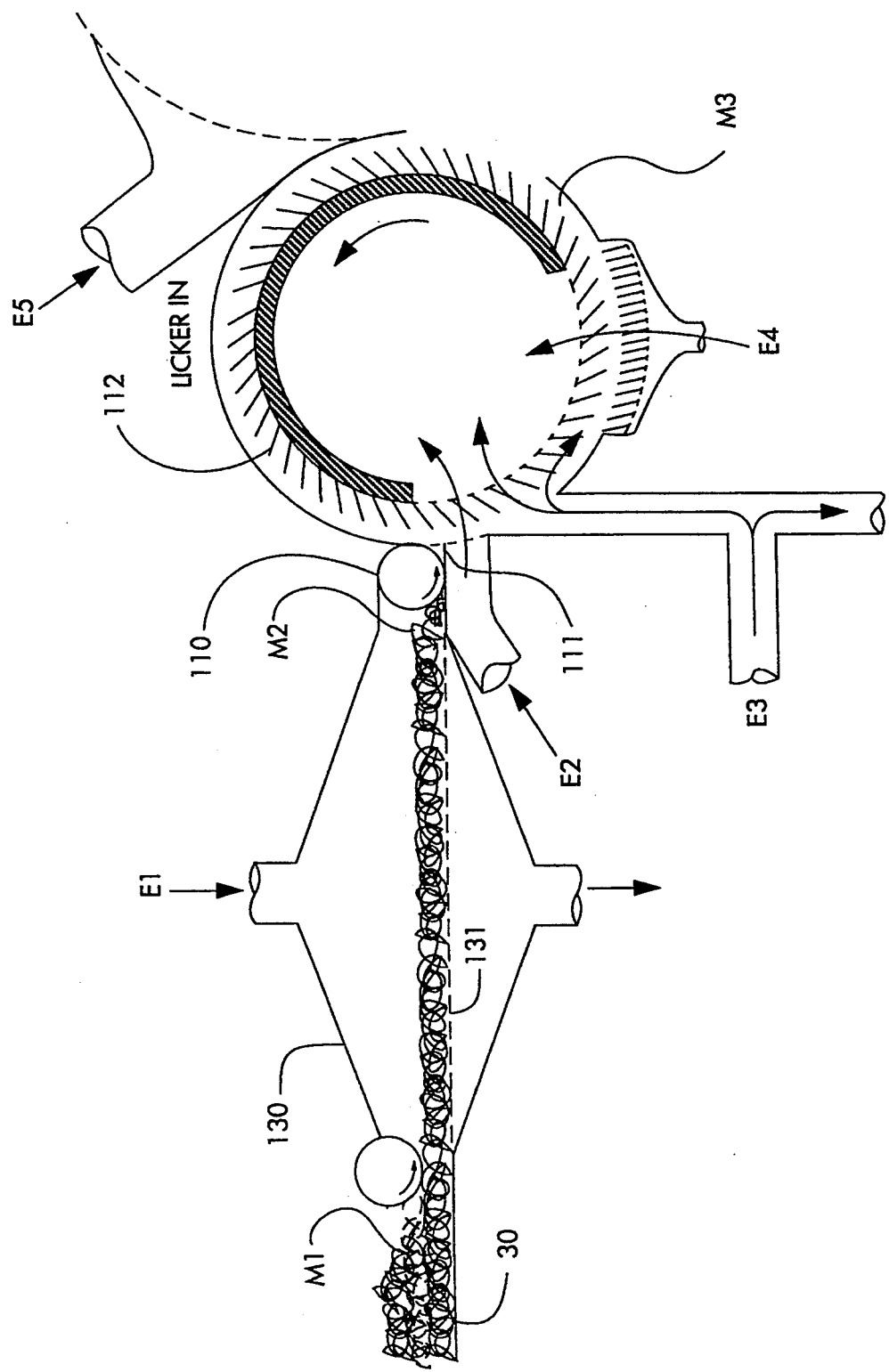
FIG. 7 is an enlarged portion of the feed end of the FIG. 6 carding stage.
Figure 8:
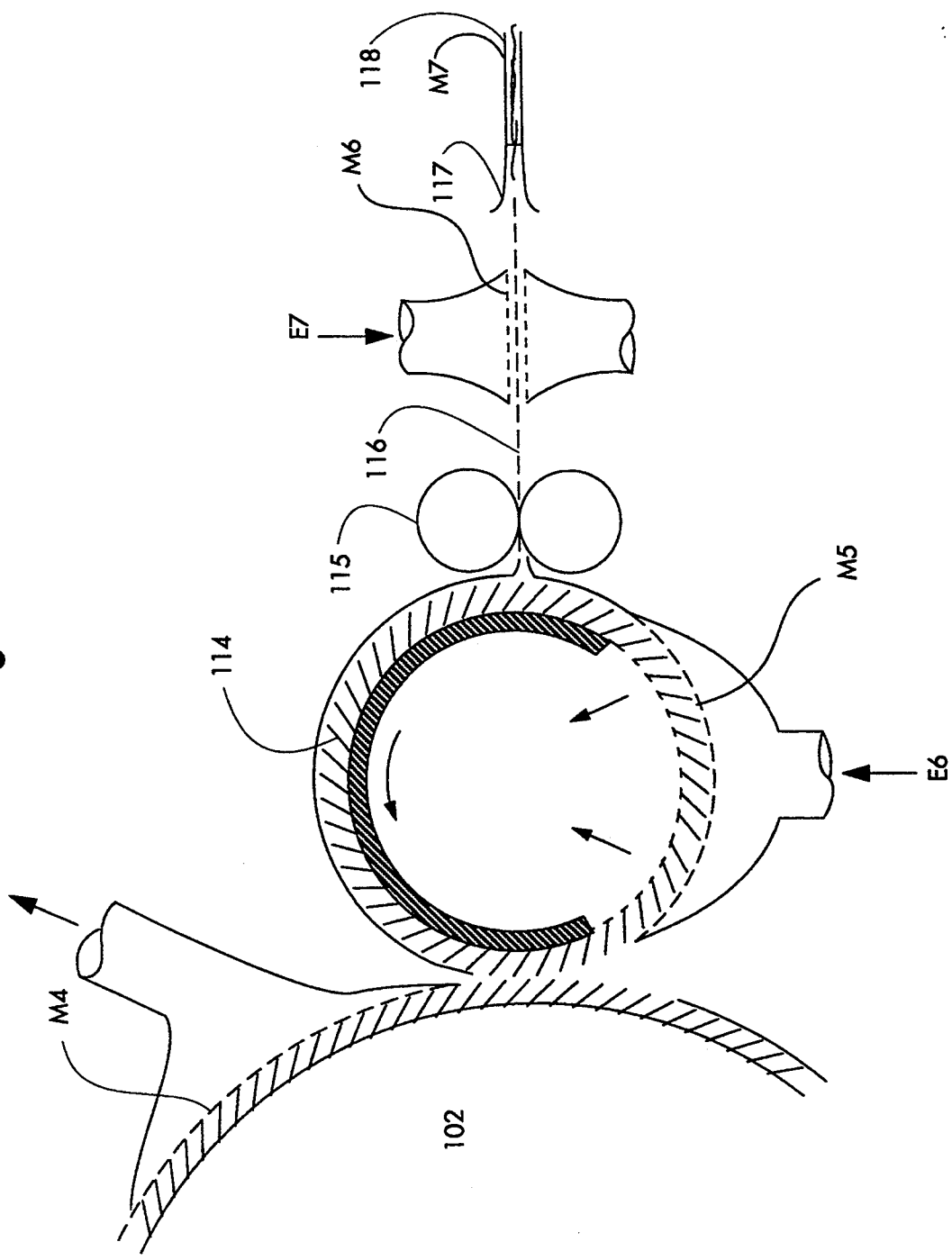
FIG. 8 is an enlarged portion of the doffer end of the FIG. 6 card.

With reference now to FIGS. 6–9, by way of example a particular application of the invention with reference to a card, such as the FIG. 5 card 24, will now be described. FIG. 6 depicts a carding stage 100 in overview, FIG. 7 is an enlarged view of the feed or licker-in section of the FIG. 6 carding stage 100, and FIG. 8 is an enlarged view of the doffer or exit portion of the FIG. 6 carding stage 100.

At the outset, it may be noted that the carding stage 100 is generally conventional, but is modified to include various measuring stations or sensors ("M" prefix), as well as environmental control stations ("E" prefix), where conditioned gas flows are applied.

Central to the card stage 100 is a card cylinder 102 covered with card wire 104 of conventional construction, and rotating with a circumferential velocity of, for example, 10 meters per second. Closely adjacent to the card cylinder 102 are a plurality of card flats 106.

Fiber stock 30 is conveyed along a perforated plate 108, and reaches a feedroll 110 which transfers the fiber to a licker-in cylinder 112, in the process. The licker-in cylinder 112 rotates for example at a circumferential velocity of 20 meters per second, and in turn transfers the fiber to the rotating card cylinder 102, where it is subjected to combing action between the carded wire 104 and flats 106.

A rotating doffer cylinder 114 removes the carded fibers from the rotating card cylinder 102, to produce a web 116. Web 116 is approximately one meter in width and has a linear density of about 5 grams per meter. Trumpet 117 collects the web and forms it into a sliver 118 whose linear density is also about 5 grams per meter, whose diameter following the trumpet is about one centimeter, and whose delivery speed is about two meters per second.

In an implementation of the invention, the carding stage 100 is modified to include the mounting of the measuring stations at critical points, such as, but not limited to, measuring station M1 where fiber stock 30 is supplied to the card, M2 where fiber stock is taken up by the feedroll 110, M3 where fiber is on the licker-in cylinder 112, M4 where fiber is on the card cylinder 102, M5 where fiber is on the doffer cylinder 114, and M6 and M7 where characteristics of the web 116 or sliver 118 are measured, respectively.

The environmental control stations represent points where conditioned gas flow is applied, for example in using any of the techniques disclosed in the above-identified Shofner U.S. Pat. Nos. 4,512,060, 4,631,781 and 4,686,744. Thus as examples, a suitable upper plenum 130 generally encloses the fiber material moving along the perforated feed plate 108, and a conditioned gas flow introduced at environmental control station E1 acts on fiber conveyed along the perforated feed plate 108. Flow E1 is pulled through the fiber mat 30 by suction applied to lower hood 131 and perforated feed plate 108. Preferably, the licker-in cylinder 102 is perforated and conditioned flows are introduced as at E2, E3 and E4 to serve the dual purposes of conditioning the fiber and aiding in the extraction of dust, trash and microdust in the manner disclosed in the above-identified Shofner U.S. Pat. Nos. 4,512,060, 4,631,781 and 4,686,744. Station E5 introduces conditioned gas to fiber on the card cylinder 102, and environmental control station E6 introduces conditioned gas to fiber on the doffer cylinder 114 which may also be perforated, as shown in FIGS. 6 and 8. Environmental control station E7 introduces conditioned gas to the web 116 leaving the crush rolls 115.

A specific example will now be considered illustrating the concepts of the invention.

At measuring station M2 where fiber is about to enter the licker-in cylinder 112, moisture content, trash and short fiber content are all measured. Numerous other processing performance parameters can be measured. By way of example, moisture content may be 5%, trash may be 500 particles per gram, and short fiber content 8%. At M5 or M6, short fiber content and trash content at the output of the card are measured.

This is a simplified example, and we consider only one controlling parameter, namely, moisture or water applied at environmental control station E1 to control the absolute humidity of the gas flow. Numerous other controlling parameters and points of their application can be used. The absolute humidity at E1 can be influenced in any way, for example, by ultrasonic humidification, spray nozzles, or steam injection. Relative humidity can be influenced by temperature control. Humidity at E1 controls moisture content at M2, which in turn controls trash and short fiber content at M5, as is discussed in detail hereinbelow. As an example, relative humidity at E1 may be 50%.

Figure 9:
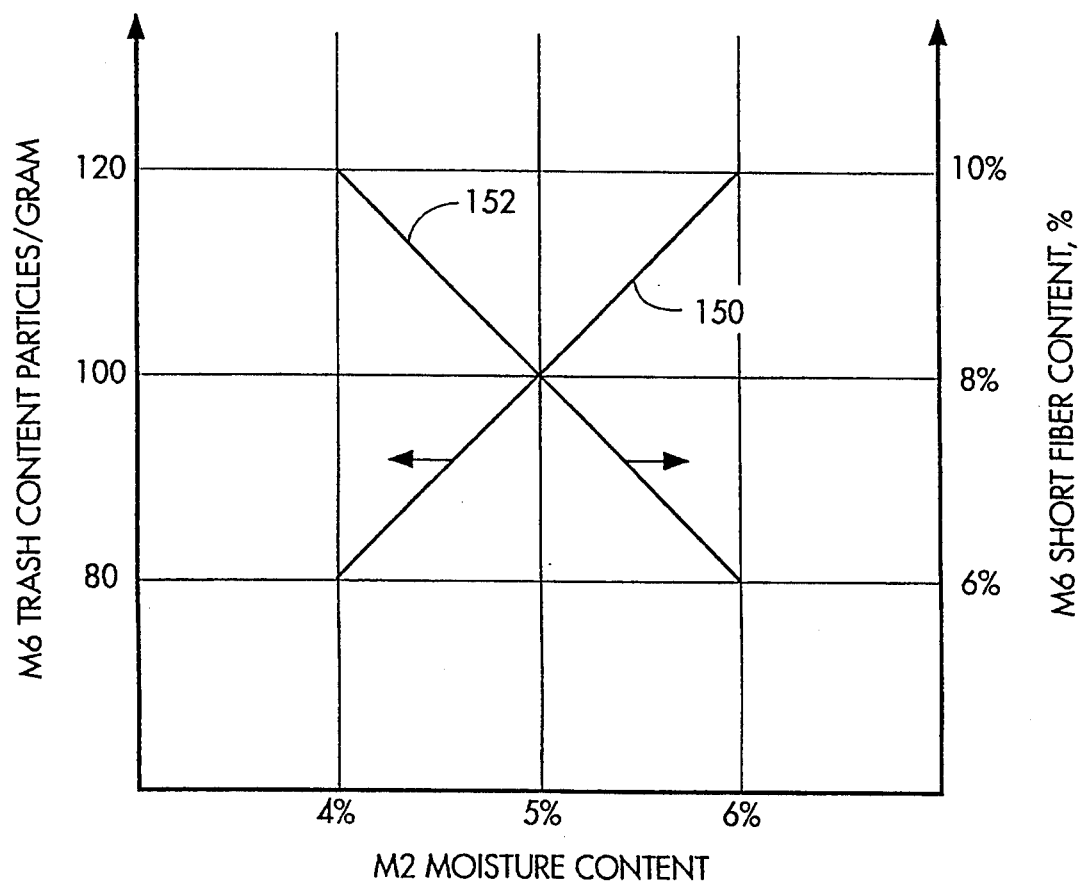
FIG. 9 is a plot depicting conflicting machine performance parameters.

Moisture content, as measured at M2, affects both the trash content and the short fiber content as measured at M6, but in conflicting manners. The conflict is plotted in simplified form in FIG. 9. The abscissa of FIG. 9 is moisture content as measured at M2 and is controlled directly through conditioning of the gas introduced at E1. The left ordinate is trash as measured at measuring station M6 and plotted as line 150. The right ordinate is short fiber content in percent by weight of fibers whose length is less than ½ inch, plotted as line 152. Monitoring station M6 may be the image analysis system described in concurrently-filed Shofner et al application Ser. No. 07/999,114, filed Dec., 31, 1992, entitled "Acquisition, Measurement, and Control of Thin Webs of In-Process Textile Materials".

In this example, there is a nominal operating point of 100 trash particles per gram, which is associated with a moisture content at M2 of 5%. As moisture content increases, trash content also increases, and trash content decreases as moisture content decreases. In this somewhat arbitrary example, at a 4% moisture content the resultant trash content is 80 trash particles per gram, and at a 6% moisture content, the trash content is 120 particles per gram. In general, it is desirable to minimize trash content.

Considering the short fiber content, at the nominal 5% moisture content point, short fiber content in this example is 8%. As moisture content decreases, short fiber content undesirably increases, due to increased damage by the card because the fibers are weaker. Conversely, as moisture content increases, short fiber content decreases. Thus, the relationship is an inverse one. In this particular example, a moisture content of 6% results in a 6% short fiber content, while a moisture content of 4% results in a short fiber content of 10%.

From FIG. 9, it is apparent that the processing performance parameters of short fiber content and trash content are in conflict, and it is an important aspect of the invention to appropriately control both of these exemplary parameters in an optimized manner.

Consider now that the machine is operating with a given supply of cotton and, for purposes of initial reference, is operating at a trash content at M5 at 100 per gram, and a short fiber content of 8% at M5. Input fiber parameters as measured at M2 are 500 per gram for trash, and 8% short fiber content. Since the card 102 can both remove and generate short fibers, its net impact in this example is described by an efficiency of unity. Card 102 decreases the trash content from 500 per gram down to 100 per gram and thus has a trash removal efficiency of 0.80.

Assume a change, for example caused by some change in the nature of the cotton fiber 30 being introduced into the machine. By way of particular example, assume that the trash content measured at M2 increases from 500 per gram to 1000 counts per gram, and that short fiber content remains at 8%. Assuming the process is linear, trash content measured at M6 would go from 100 per gram to 200 per gram, at the same moisture content of 5%, all other things being equal.

In accordance with the invention, what is controlled is not the 5% moisture content at M2, nor the 50% relative humidity at E1; what is controlled is the processing performance of the machine, in this case the output or sliver parameters trash content and short fiber content.

In accordance with the modern statistical control methodology described in the above-referenced copending application, a suitable compromise can be developed and implemented, based on analysis of a particular machine. Such a control system would function, for example, as follows.

The control system could, for example, reduce the moisture content as measured at M2 from 5% to 4% by reducing the humidity of the air introduced at E1 as required. From FIG. 9, we would expect a 20% reduction in trash content. Trash of 200 counts per gram would accordingly be decreased to 160 counts per gram. However, if the moisture content at M2 is decreased to 4%, the short fiber content as measured at M5 goes from 8% to 10%. Thus, a difficult choice is faced, namely, whether reducing trash content to 160 counts per gram M6 has more positive impact on gross profit of the entire process than the negative impact of increasing the short fiber content to 10%. The impact on gross profit might in reality be positive since the higher trash content material can be purchased at lower cost and the value of yarn ultimately produced may be affected only slightly. On the other hand, increased short fiber content degrades yarn strength and uniformity and the marketplace treats such degradations harshly.

Thus, the system can respond in several different ways. In whatever event, a computer associated with the feedback control system appropriately programmed in accordance with modern statistical control methods, is searching all the time for what the optimum value would be for short fiber content in view of trash content, to reach a level of compromise encompassing yarn value, as well as other performance standards.

In a typical case, the operator of the machine would choose to accept a higher level of trash content in order to minimize short fiber content, and thus would program the control system to not reduce the moisture content to such a degree. The penalty in the marketplace for short fiber content is generally more severe than the penalty for trash content because short fiber content degrades yarn strength and evenness.

In summary, it is desirable to minimize the short fiber content, and it is also desirable to minimize the trash content. Yarn value is adversely affected by a high percent content of either trash or short fiber content, the value being reduced more by high short fiber than by trash content. Therefore, a tradeoff is often found to be valuable, and the optimum moisture content is therefore a compromise level to optimize yarn value. Thus, it is desirable to change the air supply conditions to specific points on a carding machine to satisfy the results of fiber cleaning and short fiber elimination.

Multiple control points may be employed. For example, in addition to E1, E4 and E5 may be utilized. It is recognized that fiber damage occurs at two points in particular, where the feedroll 110 delivers fiber to the licker-in cylinder 112, and where the fibers entertain vigorous carding action between to the card cylinder 102 and the card flats 106. Thus, relatively low moisture content fiber at M2 can be introduced to the licker-in cylinder 102 for enhanced cleaning at that point where pins on the licker-in cylinder 112 impact the fibers as they come over the feedroll 110 and feed plate 111. This increased damage is offset, however, by decreasing damage associated with the card cylinder 102 and flats 106 by introducing humid air through E4 and E5.

Similarly, in anticipation of subsequent processing, at E6 and E7 moisture content can be elevated as desired. For example, a higher moisture content would be desirable for feeding a draw frame or ultimately, a rotor spinning machine.

Figure 10:
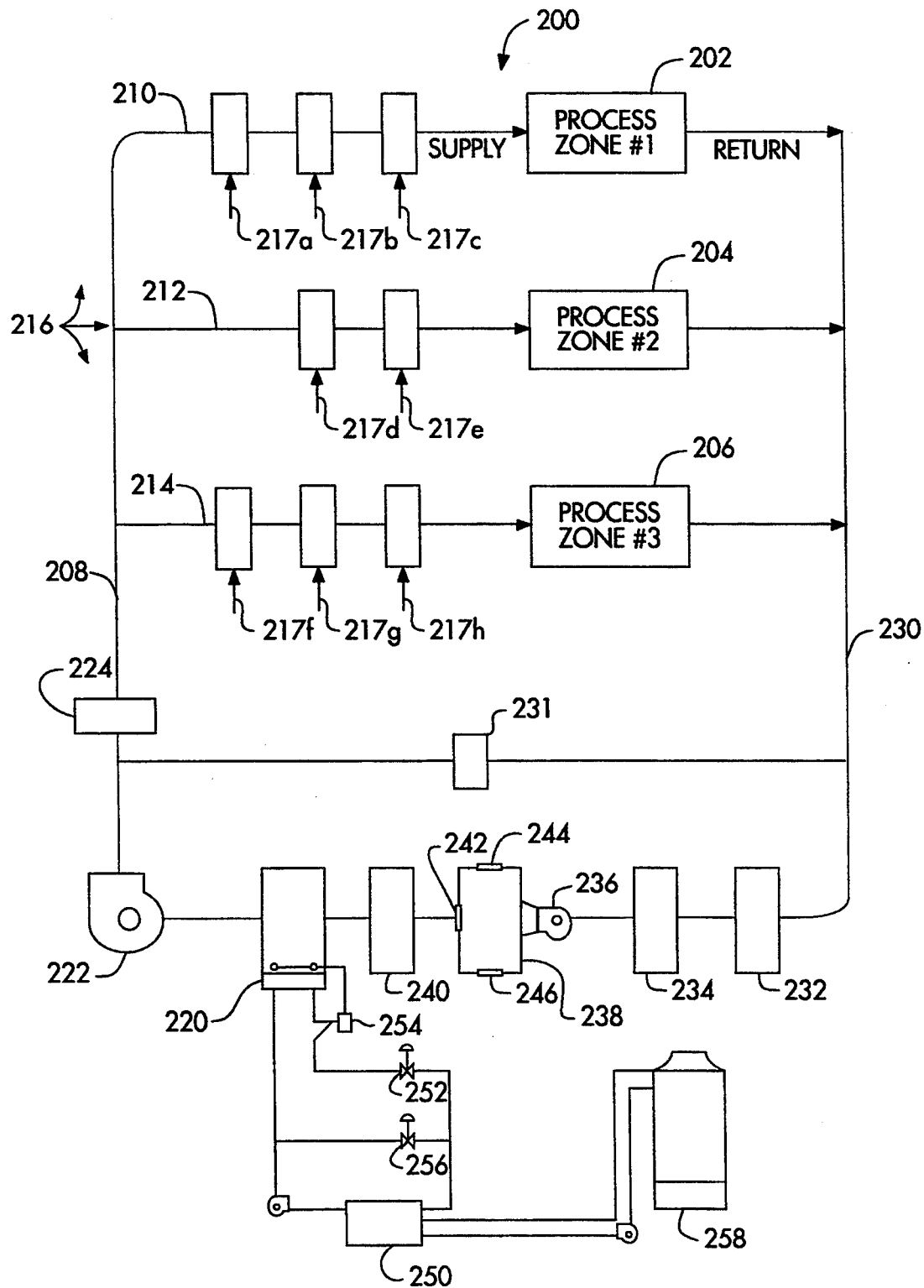
FIG. 10 is a diagram of a gas conditioning system.

FIG. 10 illustrates in overview a gas flow conditioning system for supplying conditioned air at three selected points on the FIG. 6 card 100, selected, for example, among the environmental stations designated E1, E2, E3, E4, E5, E6 and E7. For convenience of illustration, only three process zones are shown in FIG. 10, respectively designated 202, 204 and 206. There is a common supply duct 208 with respective branches 210, 212 and 214. In series with each of the branches 210, 212 and 214 are appropriate control elements, collectively designated 216, which may comprise elements such as dampers, heater coils, humidifiers, filters or ion grids.

Central to the supply system is an air washer 220, for example an air washer available from Pneumafil Corp., Charlotte, N.C. or Luwa-Bahnson, Winston-Salem, N.C. The air washer 220, with appropriate control components, provides an air flow of a predetermined initial humidity, as determined to be appropriate for the system. This air flow is driven by a blower 222 through a volume damper 224 into the supply duct 208, which supplies individual branches 210, 212 and 214. The supply air fan 222 thus furnishes air to the three or more points on the card, as further modified by the control elements 216 and in response to control signals 217a, 217b, etc.

Suction or return air from the card process zones, plus any air by-passed through damper 231, is collected by a duct 230, and is cleaned by a two-stage filter comprising a primary filter 232 and a secondary filter 234 in the form of a drum or roll filter. Return air blower 236 draws air from the filters 232 and 234 and delivers the return air into a mixing plenum 238, which may optionally be followed by a tertiary filter 240, which then delivers cleaned air to the air washer 220.

The mixing plenum 238 and return air fan 236 in particular would be provided in situations when it is desirable to operate the system on an economy cycle, avoiding the need for a chilled water or other cooling system when outside air conditions allow the maintenance of the desired temperature of the air flow by means of evaporative cooling. The mixing plenum 238 accordingly has associated with it return air dampers 242, outside air dampers 244, and exhaust air dampers 246.

In hot weather, or when outdoor conditions will not allow the maintenance of the required temperature without additional cooling, a chilled water cooler 250, for example a unit supplied by the Trane Company, can be employed to provide control of the spray water temperature, and thus the temperatures and/or humidity of the supply air or gas via control of a chilled water supply valve 252, which allows chilled water to enter an air washer recirculating pump 254. Another valve 256 is provided to assure a constant flow of water through the water chiller, averting possible freeze up conditions.

In lieu of spraying chilled water in the air washer, a "closed loop" chilled water system may be utilized, whereby the cooling effect is achieved by means of coils located in the air stream to be conditioned, through which chilled water is circulated as required to achieve the desired conditions. Associated with the unit 250 is a cooling tower 258.

While specific embodiments of the invention have been illustrated and described herein, it is realized that numerous modifications and changes will occur to those skilled in the art. It is therefore to be understood that the appended claims are intended to cover all such modifications as fall within the true spirit and scope of the invention.

What is claimed is:

1. A method for processing fiber in a machine comprising:
    measuring a plurality of processing performance parameters; and
    controlling the plurality of processing performance parameters in accordance with a predetermined optimal control strategy by deliberately applying a gas flow conditioned by at least one controlling parameter.

2. A method for processing fiber in a machine comprising:
    measuring at least one processing performance parameter selected from the group consisting of trash content, nep content, short fiber content, trash removal efficiency, nep removal efficiency, short fiber removal efficiency, machine production efficiency, and fiber value; and
    controlling the at least one processing performance parameter by deliberately applying a gas flow conditioned by at least one controlling parameter.

3. A method in accordance with claim 1, wherein the at least one controlling parameter is selected from the group consisting of humidity, temperature, ion content, velocity, velocity fluctuations, pressure, pressure fluctuations, gas composition and radioactive particle concentration.

4. A method in accordance with claim 1, wherein the at least one controlling parameter is selected from the group consisting of humidity, temperature, ion content, velocity, pressure fluctuations, gas composition, and radioactive particle concentration.

5. A method in accordance with claim 1, which comprises controlling a plurality of processing performance parameters in accordance with a predetermined optimal control strategy.

6. A method in accordance with claim 4, which comprises controlling a plurality of processing performance parameters in accordance with a predetermined optimal control strategy.

7. A method in accordance with claim 1, which comprises processing the fiber by subjecting the fiber to carding action.

8. A method for processing fiber in a machine having a plurality of processing stages, said method comprising:
    for each of the processing stages, measuring at least one processing performance parameter; and
    controlling the at least one processing performance parameter for each of the processing stages by deliberately applying at a point appropriate for the particular stage a gas flow conditioned by at least one controlling parameter.

9. A method in accordance with claim 8, which comprises controlling for at least one of the processing stages a plurality of processing performance parameters in accordance with a predetermined optimal control strategy.

10. A method in accordance with claim 8, wherein the at least one processing performance parameter at each processing stage is selected from the group consisting of trash content, nep content, short fiber content, trash removal efficiency, nep removal efficiency, short fiber removal efficiency, and machine production efficiency.

11. A method in accordance with claim 8, wherein the at least one controlling parameter for each of the processing stages is selected from the group consisting of humidity, temperature, ion content, velocity, velocity fluctuations, pressure, pressure fluctuations, gas composition, and radioactive particle concentration.

12. A method in accordance with claim 10, wherein the at least one processing performance parameter at each processing stage is selected from the group consisting of trash content, nep content, short fiber content, trash removal efficiency, nep removal efficiency, short fiber removal efficiency, and machine production efficiency.

13. A method in accordance with claim 10, which comprises controlling for at least one of the processing stages a plurality of processing performance parameters in accordance with a predetermined optimal control strategy.

14. A method in accordance with claim 12, which comprises controlling for at least one of the processing stages a plurality of processing performance parameters in accordance with a predetermined optimal control strategy.

15. A method in accordance with claim 8, which comprises subjecting the fiber to carding action in at least one of the processing stages.

16. Apparatus for processing fiber comprising:
fiber processing machine;
a conveying system for supplying fiber material to said fiber processing machine;
at least one sensor for measuring a plurality of processing performance parameters of said fiber processing machine;
a conditioned supply system for applying a gas flow conditioned by at least one controlling parameter which affects the processing performance parameters; and
a control system connected to said at least one sensor and to said conditioned supply system for controlling the plurality of processing performance parameters in accordance with a predetermined optimal control strategy by controlling the at least one controlling parameter.

17. Apparatus for processing fiber comprising:
a fiber processing machine;
a conveying system for supplying fiber material to said fiber processing machine;
a sensor for measuring at least one processing performance parameter of said fiber processing machine, the at least one processing performance parameter being selected from the group consisting of trash content, nep content, short fiber content, trash removal efficiency, nep removal efficiency, short fiber removal efficiency, machine production efficiency, and fiber value;
a conditioned supply system for applying a gas flow conditioned by at least one controlling parameter with affects the at least one performance parameter; and
a control system connected to said sensor and to said conditioned supply system for controlling the at least one processing performance parameter by controlling the at least one controlling parameter.

18. Apparatus in accordance with claim 16, wherein the at least one controlling parameter is selected from the group consisting of humidity, temperature, ion content, velocity, velocity fluctuations, pressure, pressure fluctuations, gas composition, and radioactive particle concentration.

19. Apparatus in accordance with claim 17, wherein the at least one controlling parameter is selected from the group consisting of humidity, temperature, ion content, velocity, pressure fluctuations, gas composition, and radioactive particle concentration.

20. Apparatus in accordance with claim 17, wherein said control system controls a plurality of processing performance parameters in accordance with a predetermined optimal control strategy.

21. Apparatus in accordance with claim 19, wherein said control system controls a plurality of processing performance parameters in accordance with a predetermined control strategy.

22. Apparatus in accordance with claim 16, wherein said fiber processing machine comprises a carding machine.

23. Apparatus for processing fiber comprising:
a fiber processing machine having a plurality of processing stages;
a conveying system for supplying fiber material to said fiber processing machine;
a sensor for each of said processing stages for measuring at least one processing performance parameter;
respective conditioned supply systems for applying at a point appropriate for each stage a gas flow conditioned by at least one controlling parameter which affects the at least one processing performance parameter for the particular stage; and
a control system connected to each of said sensors and to each of said conditioned supply systems for controlling the at least one processing performance parameter for each of said processing stages by controlling the at least one controlling parameter for each particular stage.

24. Apparatus in accordance with claim 23, wherein said control system controls a plurality of processing performance parameters for at least one of said processing stages in accordance with a predetermined optimal control strategy.

25. Apparatus in accordance with claim 23, wherein the at least one processing performance parameter at each processing stage is selected from the group consisting of trash content, nep content, short fiber content, trash removal efficiency, nep removal efficiency, short fiber removal efficiency, and machine production efficiency.

26. Apparatus in accordance with claim 23, wherein the at least one controlling parameter for each of said processing stages is selected from the group consisting of humidity, temperature, velocity, pressure, velocity fluctuations, pressure fluctuations, gas composition, free charge concentration, static charge, and radioactive particle concentration.

27. Apparatus in accordance with claim 25, wherein the at least one processing performance parameter at each processing stage is selected from the group consisting of trash content, nep content, short fiber content, trash removal efficiency, nep removal efficiency, short fiber removal efficiency, and machine production efficiency.

28. Apparatus in accordance with claim 25, wherein said control system controls a plurality of processing performance parameters for at least one of said processing stages in accordance with a predetermined control strategy.

29. Apparatus in accordance with claim 27, wherein said control system controls a plurality of processing performance parameters for at least one of said processing stages in accordance with a predetermined control strategy.

30. Apparatus in accordance with claims 25, wherein at least one of said processing stages comprises a card.

* * * * *